United States Patent [19]

Hallworth et al.

[11] 4,206,758
[45] Jun. 10, 1980

[54] DEVICE FOR DISPENSING MEDICAMENTS

[75] Inventors: Gerald W. Hallworth, Ware; David Clough, Bishop's Stortford, both of England

[73] Assignee: Allen & Hanburys Limited, Bethnal Green, United Kingdom

[21] Appl. No.: 898,708

[22] Filed: Apr. 24, 1978

[30] Foreign Application Priority Data

Apr. 29, 1977 [GB] United Kingdom ............... 17976/77
Jan. 11, 1978 [GB] United Kingdom ................. 1053/78

[51] Int. Cl.² .......................................... A61M 15/00
[52] U.S. Cl. ........................... 128/203.15; 128/203.21; 128/203.23
[58] Field of Search ...................... 128/266, 206, 208; 222/193

[56] References Cited
U.S. PATENT DOCUMENTS 4,117,844  10/1978  James ................................. 128/266

Primary Examiner—Henry J. Recla
Attorney, Agent, or Firm—McAulay, Fields, Fisher & Goldstein

[57] ABSTRACT

An inhalation device by which powdered medicaments can be orally or nasally inhaled by a patient through a nozzle. A hollow body shell has a chamber therein. An air inlet leads into the chamber. A capsule retaining means has an inlet opening outside the chamber through which the capsule can be inserted. The retaining means is arranged to retain an inserted capsule with a portion of the capsule body projecting into the chamber as well as to squeeze and deform the overlapping portions of the capsule body and capsule cap. A capsule opening means is located inside the chamber. Said opening means and said retaining means are relatively movable and are so disposed that relative movement between them brings the projecting portion of an inserted capsule and the opening means into engagement with one another so as to separate the capsule body from the capsule cap. A guard prevents the separated capsule body from passing through the nozzle.

7 Claims, 7 Drawing Figures

DEVICE FOR DISPENSING MEDICAMENTS

BACKGROUND OF THE INVENTION

It is well known to administer powdered medicaments to the lung bronchioles of a patient by means of inhalation devices having mouthpieces which enable the medicament to be inhaled through the mouth of the patient. The medicament is supplied in gelatine capsules which are inserted in the device and pierced or perforated after which inhalation through the mouthpiece will cause the powdered medicament to be released from the capsule and passed to the patient.

Capsules containing such medicaments are generally of gelatine and of elongated "torpedo" shape and are constructed in two parts, one of which (called the capsule body) is partly enclosed within the other (called the capsule cap). The contacting portions of the two capsule parts are often provided with grooves and/or ribs which have the effect of "locking" the two capsule parts together. The inhalation devices for use with such capsules normally have a chamber arranged to receive a capsule containing the medicament. An air inlet aperture, or a plurality of such apertures, lead into the chamber and air from the chamber can be inhaled through a nozzle forming part of the chamber. The air inlet aperture or apertures is/are so arranged that the air flow caused by inhalation through the nozzle will cause the contents of the pierced or perforated capsule within the chamber to be released and withdrawn through the nozzle.

An object of the present invention is to provide an improved inhalation device which is simpler to operate than known devices.

SUMMARY OF THE INVENTION

An inhalation device for use in administering medicaments from capsules of the kind having a capsule body and a capsule cap which partly overlaps the capsule body comprises a hollow body shell having a chamber therein and having an air inlet into the chamber; a nozzle through which a patient can inhale air from the chamber; a capsule retaining means having an inlet opening outside the chamber through which the capsule can be inserted and being arranged to retain an inserted capsule with a portion of the capsule body projecting into the chamber as well as to squeeze and deform the overlapping portions of the capsule body and capsule cap thereby to weaken or break the lock between the capsule body and the capsule cap; capsule opening means located inside the chamber; said opening means and the said retaining means being relatively movable and being so disposed that relative movement between them would bring the projecting body portion of an inserted capsule and the opening means into engagement with one another thereby to separate the capsule body from the capsule cap, and a guard for preventing the separated capsule body from passing through the nozzle when air is aspirated therethrough.

In one embodiment the hollow bodyshell is a cylinder which is open at one end and closed at the other, a closure sleeve is rotatably fitted to the open end of the shell, the said closure sleeve being provided with the nozzle and with the capsule retaining means and the said opening means being so located in the chamber that rotation of the sleeve with respect to the body shell will bring the projecting portion of a capsule inserted in the retaining means into engagement with the opening means thereby to separate the capsule body from the capsule cap. The capsule opening means may be an abutment extending into the chamber and the retaining means is a tube having an inlet opening at the end of the closure sleeve and disposed so that the projecting portion of a capsule inserted in the tube will extend longitudinally into the chamber in a position to engage the side of the rib when the sleeve is rotated with respect to the body shell.

In another embodiment, the body shell has the nozzle at one end and a closure sleeve is slidable on the other end of the shell, the retaining means being a tube which extends into the chamber through a longitudinal slot in the body shell and which has an inlet opening outside the sleeve and the capsule opening means is a bar extending across the interior of the chamber.

The capsule retaining means may be a tube having a passage at least a portion of which is of square cross-section with rounded corners.

DESCRIPTION OF SOME EMBODIMENTS

Figure 1:
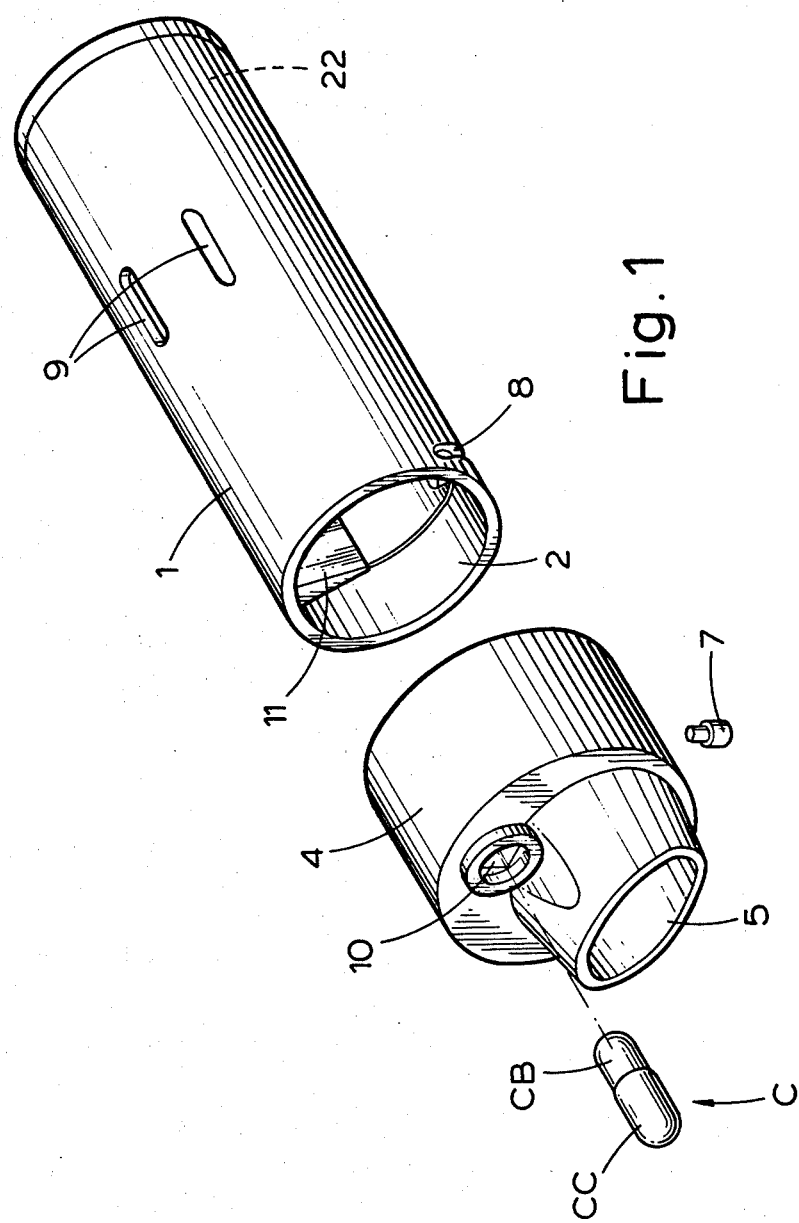
FIG. 1 is an exploded perspective view of an inhalation device.
Figure 2:
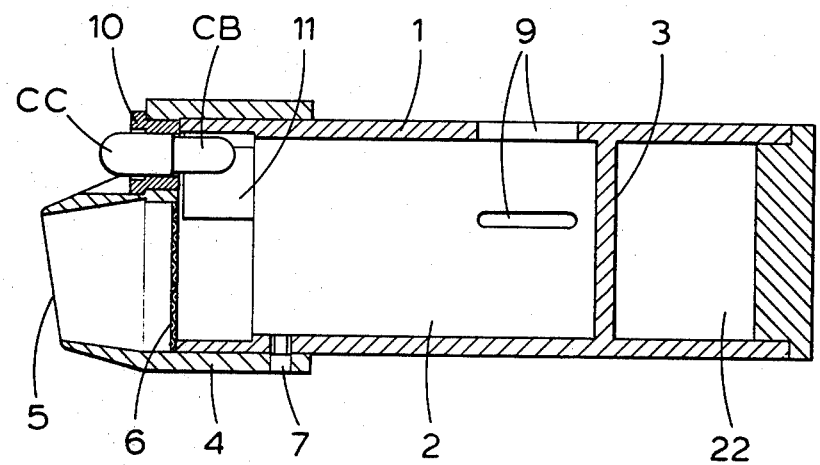
FIG. 2 is a sectional elevation of the same device.

In the embodiment of the invention illustrated in FIGS. 1 and 2 of the accompanying diagrammatic drawings, an inhalation device comprises a cylindrical body shell 1 which is conveniently, but not essentially, of a transparent plastics material. The interior of the cylindrical body shell defines a cylindrical capsule receiving chamber 2. One end 3 of the body shell is closed. Fitted at the other, or open, end of the body shell is a body closure sleeve 4 which is rotatable on the shell. This closure sleeve 4 carries a nozzle 5 which is in the form of a mouthpiece for oral inhalation. For convenience of description, the nozzle 5 is herein considered to be at the front end of the body shell and to project forwards.

A patient inhales through the nozzle to withdraw powdered medicament from the capsule receiving chamber 2 when the capsule C has been separated into two parts as hereinafter to be described. A grid or guard 6 is provided at the rear end of the nozzle to allow the powdered medicament, but not the separated capsule parts, to be withdrawn through the nozzle when the patient inhales. The closure 4 is movable axially with respect to the shell 1 and has a peg 7 (FIG. 1) or plug engaged in a screw-thread or angled slot 8 (FIG. 1) in the shell 1. As can be seen in FIG. 1, engagement of peg 7 with slot 8 will constrain peg 7 to an axially spiraling path. Thus, rotation of the closure 4, which carries peg 7, will also cause closure 4 to move axially in a spiraling path. The body shell 1 has a plurality of air inlet slots 9 running lenghtwise of the capsule receiving chamber. These slots need not extend over the full length of the chamber but may extend over only a part, say about two thirds, of the length of the periphery of the body shell.

Conveniently, there are not less than two nor more than four air inlet slots. The air inlet slots 9 communicate with the chamber 2 and are angled with respect to a diametrical chord of the chamber. Thus, when air is inhaled through the nozzle it will cause air to pass through the chamber in such a way as to agitate and rotate any part of a capsule which has been separated as hereinafter described and contained in the chamber. This will cause any powdered medicament remaining in a capsule part to be released and dispersed in the turbulent airflow and will also disperse the powder in the chamber.

The resulting dispersion will pass through the nozzle into the patient.

Figure 4:
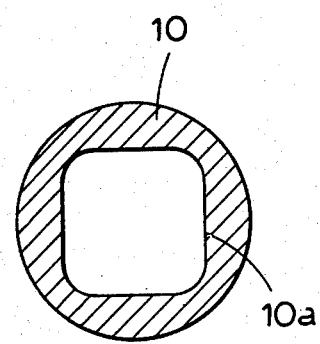
FIG. 4 is a transverse section on line A—A of FIG. 5.
Figure 5:
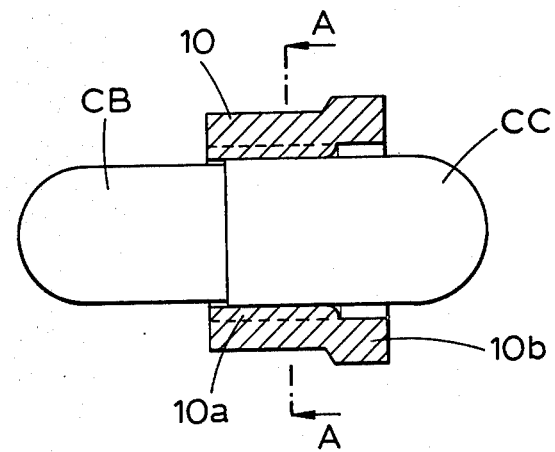
FIG. 5 is a longitudinal section of a capsule retaining sleeve of the device.

Opening at the front of the rotatable closure and adjacent the nozzle is a capsule retaining means in the form of a tube or sleeve 10 in which a capsule can be inserted. This tube or sleeve 10 is of such a length that when a capsule is pushed, body first, fully into the tube or sleeve 10, the capsule body (CB) of the capsule will protrude into the chamber 2. The tube or sleeve 10, may be a separate member fitted into the closure 4 or it may be an integral part of the closure, i.e., the closure and tube or sleeve may be a single moulding. As shown in FIGS. 4 and 5, at least part of the tube or sleeve 10 (the portion 10a) is square in cross-section with rounded corners, the remaining portion (10b) of the tube or sleeve being of greater diameter to provide a lead-in-portion for the capsule. The size and shape of the portion 10a) of the tube or sleeve 10 is such that it will squeeze and deform at least the overlapping portions of the capsule body CB and the capsule cap CC.

A capsule separating or opening member in the form of a bar, rib or other abutment 11 is located a short distance to the rear of the open end of the body shell 1. This member is conveniently of triangular or wedge shape in cross section. The member is so positioned that when a capsule is protruding from the retaining tube or sleeve 10 and the closure 4 is rotated with respect to the body shell, the protruding part of the capsule will engage the side of the member. This action will cause the two capsule parts to separate.

In operation, the body CB of a capsule C is inserted into the opening of the capsule retaining tube or sleeve 10 so as to position a portion of the capsule body in the chamber adjacent the opening member 11. The body closure 4 is then rotated on the body shell, so that the protruding portion of the capsule will engage the side of the capsule opening member. This action will remove the capsule body from the capsule cap.

The "Lock" between the capsule body and the capsule cap will have previously been weakened or broken by the insertion of the capsule body into the capsule retaining tube or sleeve in the cap. In view of the tight fit around at least the overlapping portions of the capsule cap and body in the capsule retaining tube or sleeve 10, the capsule body is deformed sufficiently to produce the desired weakening or breaking of the lock to allow the separation to be completed by the engagement of the protruding part of the capsule body with the separating or opening member. The prior breaking of the lock enables the capsule parts to be separated with less risk of permanent deformation to an extent which will significantly hinder the exit of medicament from the separated capsule parts. The separating or opening rib or bar 11 also serves to assist in emptying powder from the separated capsule body, because the capsule body repeatedly collides with the opening member when the capsule is agitated by the aspiration of air through the nozzle. The agitation and vibration produced by such collisions greatly assists the emptying operation. If desired, an additional bar or rib (not illustrated) may be provided as an additional collision or "kick" bar still further to assist in the emptying operation.

In normal operation, the capsule cap remains in the opening after the separation of the capsule. The insertion of the next capsule in the opening displaces the capsule cap of the previous capsule into the chamber and this capsule cap will normally remain in the chamber until the capsule body of the next capsule is removed from the chamber.

After the inhalation operation, the closure 4 can be removed from the body shell 1 to enable the body portion CB of the spent capsule to be removed. As shown in FIG. 1, this can easily be accomplished by removal of peg 7 to allow closure 4 to slide clear of shell 1. Alternatively, the closed or rear end of the body shell 1 can be made removable (see FIG. 2).

The capsule cap CC can be disengaged from the capsule retaining means 10 by insertion of the next capsule ready for use on another occasion.

If desired, the body shell may be extended beyond the end wall 3 to provide a storage chamber 22 for capsules into which a patient may for example, load a day's supply of capsules.

Figure 6:
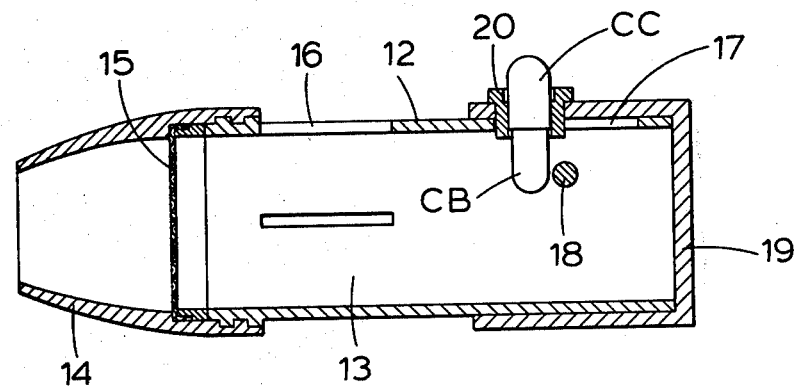
FIG. 6 is a sectional elevation of an alternative device.

In the embodiment of the invention illustrated in FIG. 6, an inhalation device comprises a cylindrical body shell 12 which is conveniently but not essentially, of a transparent plastics material. The interior of the cylindrical body shell defines a cylindrical capsule receiving chamber 13. Fitted at, or integral with, one end of the body shell 12 is a nozzle 14 which is in the form of a mouthpiece for oral inhalation. For convenience of description, the nozzle is herein considered to be at the front end of the body shell 12. A patient inhales through the nozzle 14 to withdraw powdered medicament from the capsule receiving chamber 13 when the capsule has been separated into two parts as hereinafter to be described. A grid or guard 15 is provided at the rear end of the nozzle 14 to prevent the separated part of the capsule, but not of the powdered medicament, being withdrawn through the nozzle when the patient inhales.

Figure 3:
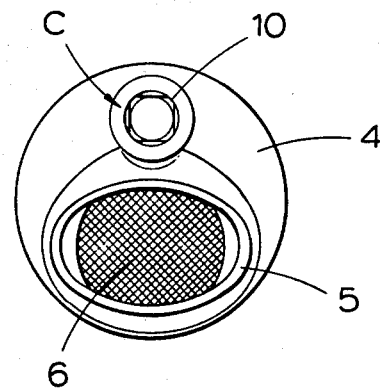
FIG. 3 is an end view.

The body shell 12 has a plurality of air inlet slots 16 running lengthwise of the capsule receiving chamber 13. As in the embodiments of FIGS. 1 to 3 these slots 16 need not extend over the full length of the chamber but may extend over only a part, say about two thirds, of the length of the periphery of the body shell. Conveniently, there are not less than two nor more than four air inlet slots. The air inlet slots communicate with the chamber and are angled with respect to a diametrical chord of the chamber. Thus, when air is inhaled through the nozzle it will cause air to pass through the chamber in such a way as to agitate and rotate any part of a separated capsule contained in the chamber. This will cause any powdered medicament remaining in a capsule part to be released and dispersed in the turbulent airflow and will also disperse the powder in the chamber.

The resulting dispersion will pass through the nozzle into the patient.

The periphery of the body shell 12 is also provided with a further slot 17, herein called a capsule entry slot, running lengthwise over a portion of the body shell 12. A capsule separating or opening bar 18 extends across the interior of the capsule receiving chamber 13 adjacent the capsule entry slot 17. An operating sleeve and closure cap 19 is slidable on the rear end portion of the body shell 12. The sleeve 19 has an internal shape and size complementary to the external shape and size of the body shell 12 and is closed by a rear end wall. A capsule retaining member 20 having an opening in which a capsule can be inserted and retained is provided in the wall of the operating sleeve 19 of similar construction to that illustrated in FIGS. 4 and 5. This member 20 is so positioned in the sleeve 19 that when the sleeve is fully slid on the body shell 12, the opening of the member 20 will register with the capsule entry slot 17 in the body shell 12. This opening is square in cross section with rounded corners.

Figure 7:
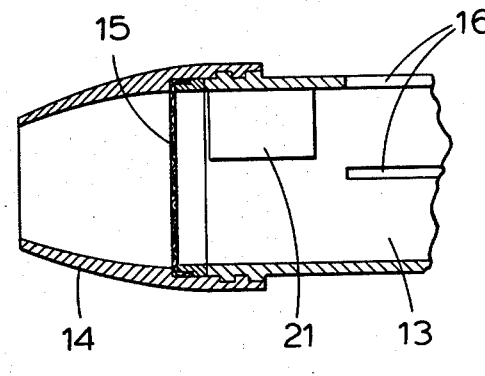
FIG. 7 is a scrap section illustrating a modification of the device illustrated in FIG. 6.

In a modification illustrated in FIG. 7, the device is provided with a collision or "kick" bar 21 against which the separated part of the capsule collides when air is inhaled through the mouthpiece 14 thereby to assist in emptying the capsule of medicament.

In operation, the sleeve 19 is closed fully on the body shell and the body of a capsule is inserted into the opening of member 20 so as to pass through the capsule entry slot 17 to position a portion of the capsule body CB in the chamber transversely of the axis of the chamber 13 and the sleeve, and in front of the bar 18. The sleeve 19 is then slid on the body shell 12 away from the nozzle 14, so that the protruding portion CB of the capsule will engage the capsule opening bar 18 in the chamber. This action will remove the capsule body CB from the capsule cap CC so that the medicament can fall into the dispersion chamber.

The "lock" between the capsule body and the capsule cap will have previously been weakened or broken by the insertion of the capsule body into the capsule retaining member 20 in the operating sleeve. In view of the tight fit around the capsule cap and body in the opening, the capsule body is deformed sufficiently to produce the desired weakening or breaking of the lock to allow the separation to be completed by the engagement of the protruding part of the capsule body with the separation bar.

In normal operation, the capsule cap remains in the opening after the separation of the capsule. The insertion of the next capsule in the opening displaces the capsule cap of the previous capsule into the chamber.

After the inhalation operation, the sleeve or mouthpiece can be removed from the body shell to enable the body portion of the spent capsule to be removed and the cap can also be disengaged from the aperture, by insertion of the next capsule ready for use on another occasion.

What is claimed is:

1. An inhalation device for use in administering medicaments from capsules of the kind having a capsule body and a capsule cap which partly overlaps the capsule body, and is secured thereto by a lock structure formed on the capsule body and cap, said device comprising:
   (a) a hollow body shell defining a chamber and having an air inlet into said chamber; a nozzle through which the patient can inhale air from said chamber;
   (b) capsule retaining means having an inlet opening outside said chamber through which the capsule can be inserted and being arranged to retain an inserted capsule with a portion of the capsule body projecting into said chamber, as well as to squeeze and deform the overlapping portions of the capsule body and capsule cap thereby to weaken or break the lock between the capsule body and the capsule cap;
   (c) capsule opening means located inside said chamber; said opening means and said retaining means being relatively movable and being so disposed that relative movement between them will bring the projecting portion of an inserted capsule and said opening means into engagement with one another thereby to separate the capsule from the capsule cap, and
   (d) a guard for preventing the separated capsule body from passing through said nozzle when air is aspirated therethrough.

2. An inhalation device as claimed in claim 1, wherein said capsule opening means is fixed inside said chamber and an operation sleeve is movable on said body shell, said sleeve being provided with said capsule retaining means.

3. An inhalation device as claimed in claim 1, wherein said hollow body shell is a cylinder which is open at one end and closed at the other, a closure sleeve is rotatably fitted to the open end of said shell, said closure sleeve being provided with said nozzle and with said capsule retaining means and said opening means being so located in said chamber that rotation of the sleeve with respect to said body shell will bring the projecting portion of a capsule inserted in said retaining means into engagement with said opening means thereby to separate the capsule body from the capsule cap.

4. An inhalation device as claimed in claim 3, wherein said capsule opening means is an abutment extending into said chamber and said retaining means is tubular and has an inlet opening at the end of said closure sleeve and disposed so that the projecting portion of a capsule inserted in said retaining means will extend longitudinally into said chamber in a position to engage the side of said abutment when said sleeve is rotated with respect to said body shell.

5. An inhalation device as claimed in claim 4, wherein said closure sleeve is axially displaceable as well as rotatable with respect to said body shell.

6. An inhalation device as claimed in claim 1, wherein said body shell has said nozzle at one end and a closure sleeve is slidable on the other end of said shell, said retaining means being tubular and extending into said chamber through a longitudinal slot in said body shell and which has an inlet opening outside said sleeve and said capsule opening means is a bar extending across the interior of said chamber.

7. An inhalation device as claimed in claim 1, wherein said capsule retaining means has a passage at least a portion of which is of square cross-section with rounded corners.

* * * * *